(12) United States Patent
Mbachu et al.

(10) Patent No.: US 6,846,447 B2
(45) Date of Patent: Jan. 25, 2005

(54) METHODS FOR MONITORING RESIN-LOADING OF WOOD MATERIALS AND ENGINEERED WOOD PRODUCTS

(75) Inventors: Reginald A. Mbachu, Eugene, OR (US); Tyler G. Congleton, Eugene, OR (US)

(73) Assignee: Dynea Chemicals Oy, Eugene, OR (US)

(*) Notice: Subject to any disclaimer, the term of this patent is extended or adjusted under 35 U.S.C. 154(b) by 9 days.

(21) Appl. No.: 10/338,069

(22) Filed: Jan. 7, 2003

(65) Prior Publication Data

US 2004/0094853 A1 May 20, 2004

Related U.S. Application Data

(63) Continuation-in-part of application No. 10/294,296, filed on Nov. 14, 2002.

(51) Int. Cl.[7] ............................................. B29C 45/76
(52) U.S. Cl. ...................... 264/406; 264/410; 264/488; 264/492; 264/40.1
(58) Field of Search ................................ 264/406, 410, 264/488, 492, 40.1; 156/64, 182, 272.2; 428/292.4, 327; 250/307

(56) References Cited

U.S. PATENT DOCUMENTS 3,196,072 A * 7/1965 Wirtz ........................ 162/198
4,508,772 A * 4/1985 Churchland et al. ........ 428/106
5,104,485 A * 4/1992 Weyer .......................... 162/49
5,619,038 A * 4/1997 Parigi et al. ............ 250/339.12
6,461,743 B1 * 10/2002 Tanzer et al. ................ 428/535

* cited by examiner

Primary Examiner—Michael P. Colaianni
Assistant Examiner—Monica A. Fontaine
(74) Attorney, Agent, or Firm—Shanley and Baker (57) ABSTRACT

Process for calibration of spectroscopic instrumentation for non-invasive monitoring of resin-loading of furnish-type wood materials, such as particles or fibers for particleboard or medium density fiberboard, respectively. Selection of ranges of wavelengths within a 350 nm to 2500 nm region by providing selection of spectrometers and sensors for wavelength ranges of 350–1000 nm, 1000 to 1800 nm, 1000 to 2500 nm, and 400 to 2200 nm, for use by engineered-wood manufacturing installations. Resin-loaded wood material is exposed to selected VIS/NIR energy and monitored as it moves on-line in relation to calibrated spectroscopic instrumentation; a sensor collects non-absorbed radiation energy reflected by the wood materials. Measurements are processed, in relation to pre-established calibration data, to determine whether the resin-loading is within manufacturing objectives; monitoring and feedback are used to maintain desired specifications.

11 Claims, 8 Drawing Sheets

METHODS FOR MONITORING RESIN-LOADING OF WOOD MATERIALS AND ENGINEERED WOOD PRODUCTS

RELATED APPLICATION

The present application is a continuation-in-part of U.S. Ser. No. 10/294,296 filed Nov. 14, 2002 entitled "NIR SPECTROSCOPIC MONITORING OF RESIN-LOADING DURING ASSEMBLY OF ENGINEERED WOOD PRODUCT", which is incorporated herein by reference.

INTRODUCTION

The present invention relates to methods and apparatus for monitoring resin-loading of wood materials during assembly for manufacture of engineered wood product. More specifically, this invention is concerned with calibration and use of spectroscopic instrumentation for quantitatively measuring resin-loading during on-line assembly of composite wood product; and, maintaining that resin-loading within manufacturing standards, in particular, during assembly of particleboard (PB) and medium-density fiberboard (MDF).

OBJECTS OF THE INVENTION

A primary object provides for calibrating spectroscopic instrumentation for accurate and prompt measurement of resin loading during assembly of wood materials prepared for manufacture of composite wood product.

A related object provides for calibrating use of spectrometers using selected wavelength ranges within the full visual (VIS) and near-infrared (NIR) wavelength region of electromagnetic radiation.

An important object provides for monitoring resin-loading of wood particulate and fiber materials during on-line assembly, respectively, of particleboard (PB) and medium-density fiberboard (MDF).

A specific object is to provide on-line measurement of resin-loaded wood materials as assembled prior to heat and pressure bonding treatment.

A further object provides for feedback of resin-loading data to maximize continuing on-line assembly within manufacturing standards and to optimize resin usage.

The above objects and other contributions of the invention are considered in more detail in describing the invention in relation to the accompanying drawings.

DETAILED DESCRIPTION OF THE INVENTION

Contributions of the invention involve uncovering opportunities for potential improvement in the assembly and manufacture of engineered wood product. Recognizing that producing quality composite wood product requires a consistent rate of application of resin was a major factor in determining that consistency in resin-loading can best be achieved by quantitative-analyses during assembly of the raw-wood material. And, also, concluding that in order to ensure product homogeneity, minimize out-of specification product, and optimize adhesive resin use, accuracy in measuring resin-loading should be carried-out while the wood material is traveling during in-line assembly.

Specific embodiments are described working with furnish-type wood-material. An adhesive resin in liquid form is atomized and directed into a chamber forming a fluidized bed for in-line movement of the wood material; and, resin application is carried out during that movement in the fluidized bed while moving at an in-line assembly rate. Specific examples of wood material include particulate wood for manufacture of particleboard (PB) and wood fibers for assembly of medium-density fiberboard (MDF). Resin-loading of the wood material is monitored following resin application in an assembly line, prior to heat and pressure bonding treatment to form commercial engineered wood product.

The above procedures provide early on-line detection of out-of-specification material, if any; and, in addition, the invention provides for adjustment of resin-loading, if any is required, to be carried out promptly to bring the resin-loading within manufacturing specifications. Promptly maintaining desired manufacturing specifications minimizes or eliminates losses in material and production rate.

It is significant that non-invasive on-line monitoring of resin-loading takes place without disturbing furnish-like wood materials during assembly. Resin measurement involves use of spectroscopic measuring instrumentation utilizing electromagnetic radiation which is absorbed by the wood material. Further, accurate measurement of resin-loading is dependent on calibration, as disclosed herein, of that instrumentation.

The term "resin-loading" is used interchangeably herein with "resin content"; and, resin-loading of particulate and fiber "furnish" is measured and indicated as a weight percentage in relation to the weight of the wood material.

For resin-loading of particleboard (PB), liquid resin is atomized for application to sawdust-type wood particulate. After non-invasive measurement of resin content, the resin-loaded particulate is then subjected to heat and pressure, in a press layout which cures the resin resulting in bonding, to produce an extended-surface-area mat, which can later be cut into commercial sizes. The present non-invasive and continuing measuring contributions are particularly advantageous for manufacturing installations carrying out bonding in a continuous-in-line press.

Figure 1:
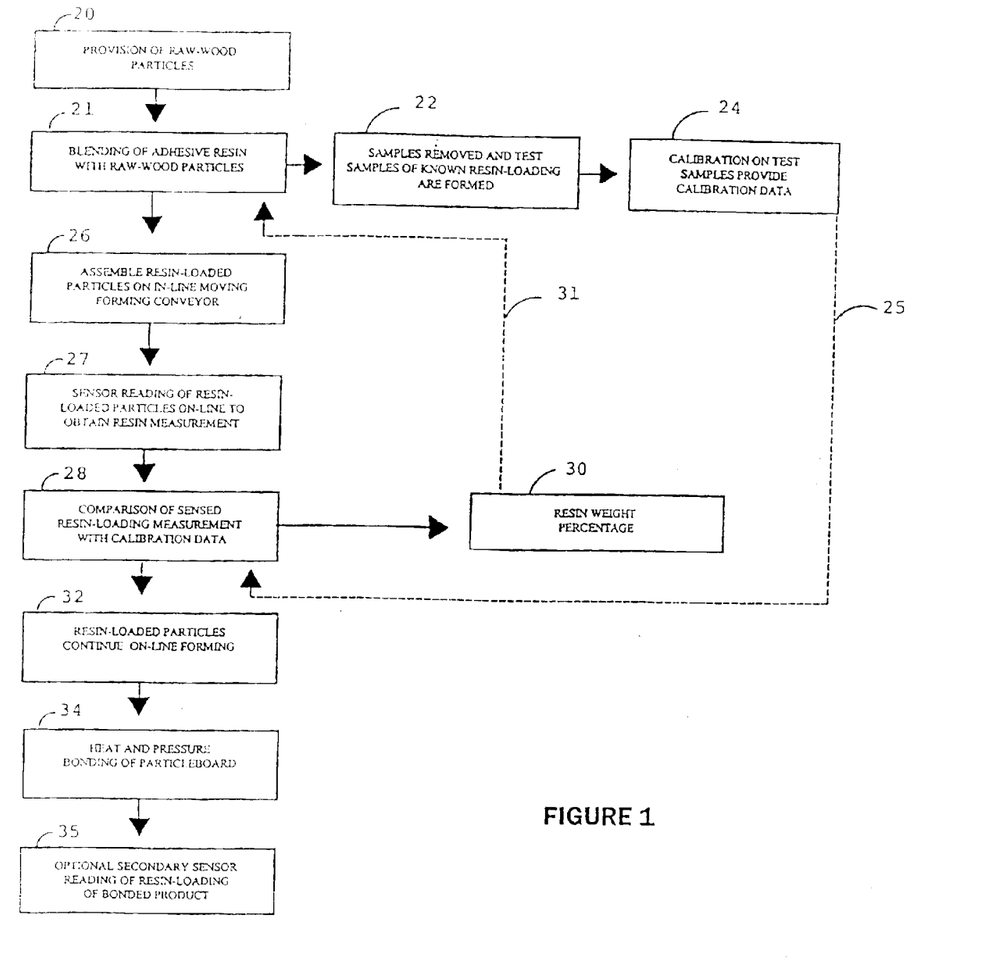
FIG. 1 is a block diagram for describing on-line assembly and processing in accordance with the invention for production of particleboard (PB)

In FIG. 1, raw-wood particulate for a particleboard (PB) embodiment is supplied at station 20; and, directed to station 21 for resin-loading with adhesive resin. Resin-loading can be carried out by feeding wood particulate into an elongated rotating chamber, or drum-like structure, extending for longitudinal travel in the assembly-line direction. The liquid resin is atomized and sprayed into the chamber to create a fluidized bed of resin; the particulate moves through that fluidized bed toward assembly.

Relating the material of interest to the measuring technique for quantitative analyses, it was discovered that, spectroscopically, resin-loading is related in a linear manner to absorption of radiation within a selected electromagnetic radiation wavelength range; and, calibration of spectroscopic instrumentation could accordingly be verified. That calibration can be initiated in an assembly line at station 22.

During calibration, in summary, wood materials of the type to be assembled are selected and accurately-predetermined resin-content reference-source test-samples are established. With furnish-type wood material, resin-loaded determinations are established by making static chemical-test measurements of the test sample materials for accurate resin-loaded weight in relation to weight of furnish. Preferably, reference-source test-samples, for calibration purposes, are resin-loaded in an incrementally progressive manner; such as: zero percent, about four percent, about eight percent, and above about twelve percent.

Calibration of spectroscopic instrumentation, within a selected range of visible (VIS) and near infrared (NIR) irradiation is carried out at station 24; calibration steps are described in more detail and graphically presented in relation to later FIGS. It has been found that the wavelength bands for moisture-content (MC) of both the wood and the resin do not effect accurate measurement of resin content; and, MC wavelength bands can be removed when the instrumentation is used to measure resin content. It should be noted that non-absorbed energy reflected by the wood materials is used to measure resin content. Calibration data, from the instrumentation used for measuring resin content, is directed from station 24 over interrupted-line 25, for use in the assembly line for the wood materials.

At station 26 in the assembly line, resin-loaded particulate is supported on an in-line conveyance system for continuing assembly of a mat of particulate, which is moving toward ultimate bonding by heat and pressure. Non-invasive capabilities for measuring of resin-loading are significantly important during assembly of wood particulate. VIS/NIR spectroscopic instrumentation for carrying out continuing non-invasive measurement is located at station 27.

A lamp with full-spectrum-light is used to illuminate the wood materials; the "red" portion of that light is absorbed by the resin. Non-absorbed radiation energy, reflected by the wood materials, is measured by the instrumentation sensor. The sensor is positioned a selected distance from the resin-loaded materials for laboratory determination of a calibration model and, also, for calibration of instrumentation being used on an assembly line. The sensor is placed above the moving materials. The illuminated and VIS/NIR irradiation covers a selected area of about three to about twenty four square inches; VIS/NIR radiation is selected in a wavelength range, made available by the invention, which penetrates the resin-loaded blend by about two to five mm.

The return reflected VIS and NIR energy is collected fiber-optically and is computer processed at station 28 to enable graphical presentation of absorbed radiation based on reflected non-absorbed radiation; instrumentation calibration data for measuring resin-loading is received, as referred to above, over interrupted-line 25 from station 24. That measurement of resin-loaded percentage weight is indicated at station 30. During production, adjustment of resin-loading percentage weight, if any is required, can be directed, manually or automatically, over interrupted-line 31 to resin-loading station 21. The rate of resin-input can be adjusted, or the assembly line-speed can be adjusted, in order to maintain uniform resin-loading; preferably the rate of resin-input is utilized.

The resin-loaded particulate at station 32 continues toward bonding at station 34. If desired, a secondary sensor can be positioned at station 35, after heat and pressure treatment, to measure resin-loading of the bonded product; station 35 can provide added confirmation that the resin bonded product is within desired manufacturing objectives.

Figure 2:
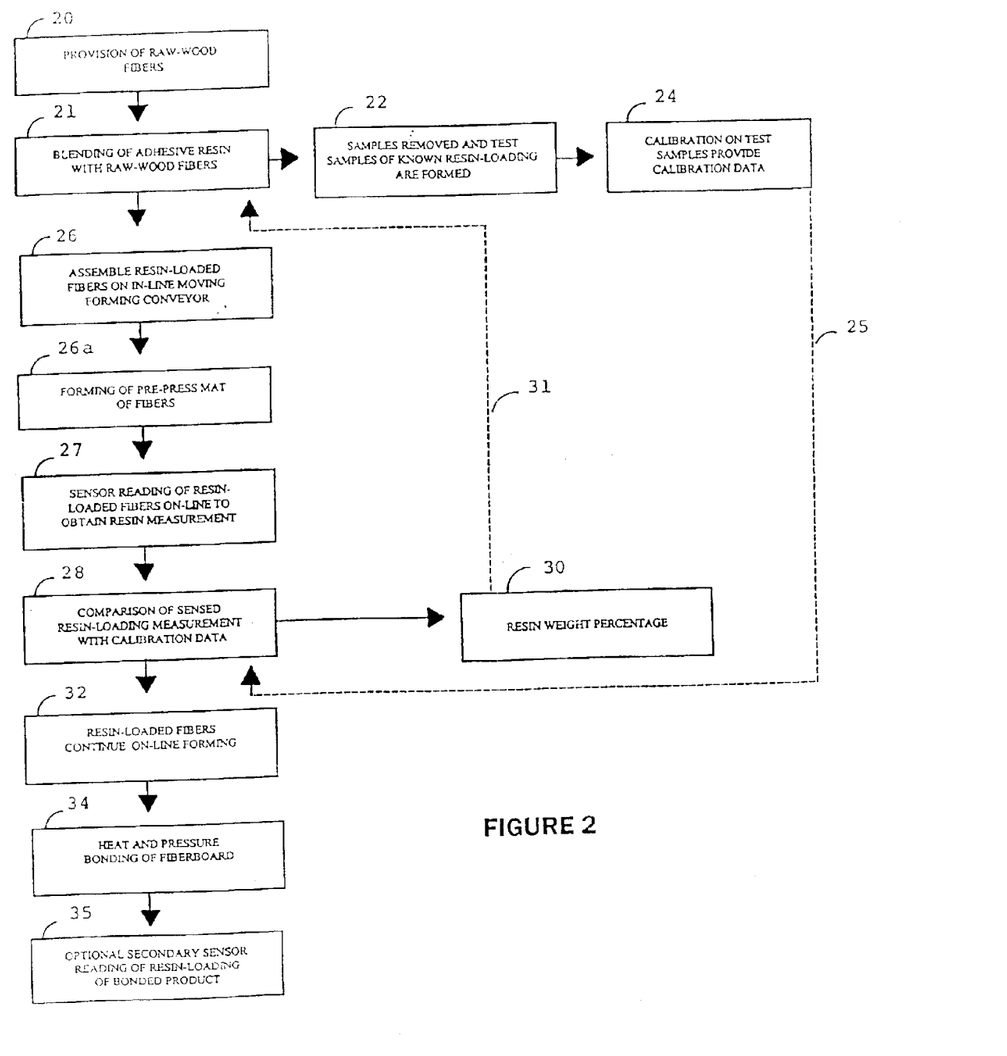
FIG. 2 is a block diagram for describing on-line assembly and processing in accordance with the invention for production of medium-density fiberboard (MDF)

Referring to FIG. 2 for assembly of MDF, a number of the method steps, as described above in relation to PB remain substantially the same for production of MDF. One difference of note for raw-wood fibers has significance. Prior to on-line calibrated monitoring of resin content, raw-wood fibers are resin-loaded. At station 26(a) of FIG. 2, a pre-press compacting of those fibers is used. Otherwise, because of the light-weight of raw-wood fibers, and the tendency to accumulate with intermediate air spacing, accurate measurements for uniformity of resin-content, throughout, can be more difficult because of the accumulated fiber height. The compacting of fibers for resin-loading measurement purposes does not require heat, and, utilizes minimum pressure to achieve desired compaction.

Other than that pre-bonding compaction of fibers, any differences in measuring resin-content between the furnish-like materials of wood particulate and wood fibers are inconsequential for purposes of carrying out the measuring methods of the invention, although the finished composite wood products are significantly different. Various types of wood for particulate for PB, or for fiber for MDF, can be used when carrying out measurements in accordance with the invention.

During calibration in a lab or on-line, accurate resin-loaded reference-source test-samples are used for establishing a calibration curve for the instrumentation. For spectroscopic quantitative analyses, a relationship between content of the material and transmittal or absorption of the radiation is the basis calibration of instrumentation. It was determined that a linear relationship exists between absorption of radiation and the amount of resin-content; and, that is used for calibration of the instrumentation. The calibration equipment of FIG. 3 to be described can be adapted for use in a lab or on-line.

Figure 3:
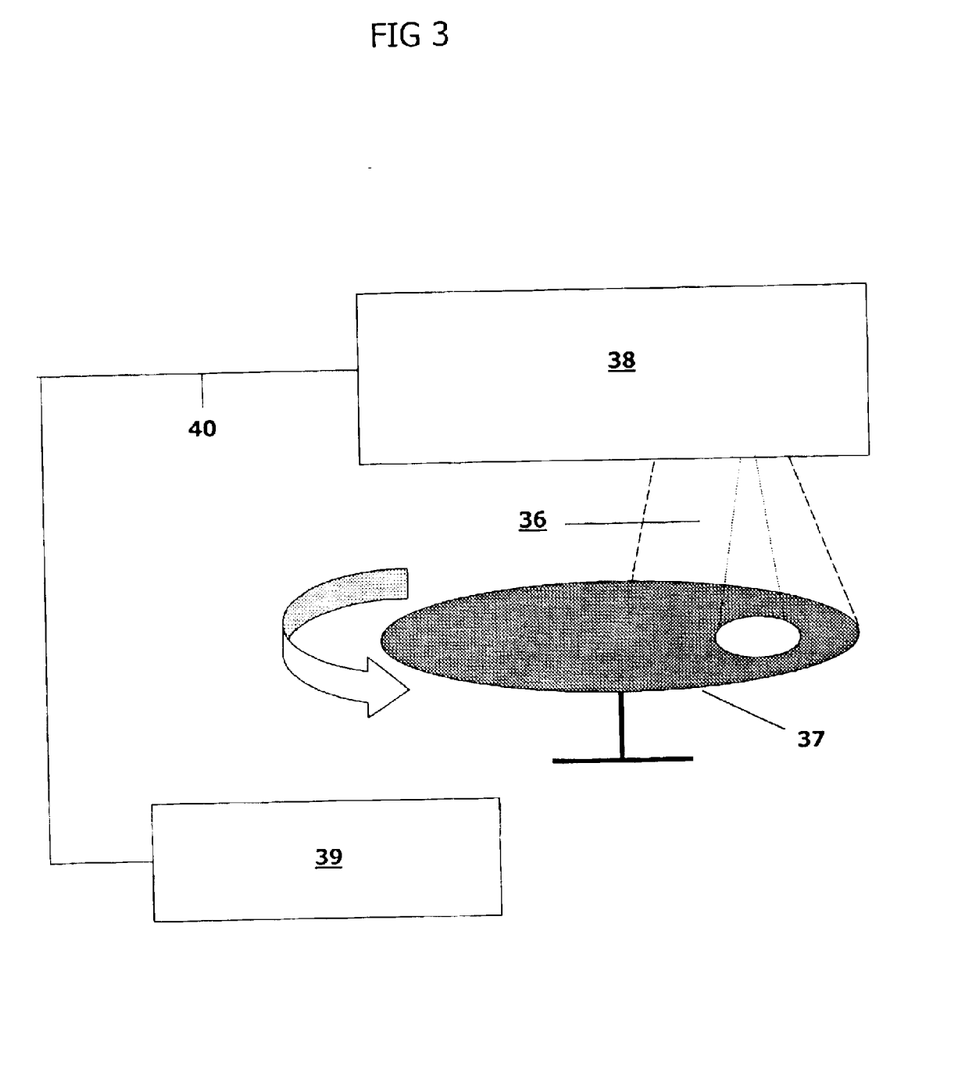
FIG. 3 is a schematic perspective view of apparatus for describing calibration steps, in accordance with the invention, for spectroscopic instrumentation.

A rotatable turntable 37, schematically illustrated in FIG. 3, is actuated so as to simulate an on-line assembly travel rate. Reference-source test-samples are supported on turntable 37, which is rotated to simulate movement of in-line material to be monitored. Calibration involves establishing the relationship between observance of spectral energy and the resin content; and can be carried out in the same manner for lab calibration or on-line calibration. However, calibration is preferably conducted for each accumulated wood material for a scheduled run of a line to be monitored since differing manufacturing specifications may apply for differing runs.

Absorption, within a selected range of VIS/NIR radiation, by the wood material is utilized. The resin-loading is determined by measuring non-absorbed VIS/NIR energy reflected by the wood material. Calibration is carried out by graphically-representing "resin content" of pre-established reference-source test-samples; based on the linear relationship of resin content to absorbed VIS/NIR. The calibration curve correlates that linear relationship, as shown graphically in later FIGS, for measurements of actual resin-loading on-line.

A unique advantage during calibration, and for on-line monitoring, is the non-invasive nature of resin-loading measuring of the furnish-type wood materials. That is, calibration of spectroscopic instrumentation, and on-line measurement of resin-loading of wood materials during assembly, can proceed without disturbing the wood materials which are resin-loaded. Of course, when on-line measurements indicate that resin-loading is not within manufacturing standards, resin-loading adjustments are made; but, again, those measurements are made without disturbing the actual assembly of furnish-type wood material.

Absorption of radiation by the resin-loaded materials can be measured by selecting a wavelength range, from the full-scale wavelength region of 350 nanometers to 2500 nanometers (nm), which provides for penetration of the wood material. A wavelength range of 400–2200 nm satisfactorily covers the above-mentioned full scale region. However, significantly, it has been discovered that acceptable standards can be maintained by other than use of full-scale, or near full-scale, wavelength regions.

It has been found that selection can be made from multiple ranges of wavelengths; an individual wavelength range can be selected from the following: (i) 350–1050 nm, (ii) 1000–1800 nm and (iii) 1000–2500 nm; those ranges and the type of sensors for measuring resin loading in each range are later tabulated herein. The resulting advantages from discovery of those multiple ranges can be important in relation to the size of composite-wood manufacturing installations.

During calibration, direct measurements are made of reference-source test samples wherein the amount of resin has been accurately pre-established. Selected peaks in the spectrum are used in calibration, which brought out that moisture content (MC) absorption wavelength band could be eliminated. That calibration data is correlated with measurements in which those samples are obtained from raw-wood material for the on-line assembly process. The apparatus of FIG. 3 can be used in a lab or for on-line calibration; an accurate linear calibration curve date is described and shown in later FIGS.

The resin-loaded wood materials are illuminated with a full visible light spectrum lamp as indicated at 36 in FIG. 3; also, a VIS/NIR source, selected from the above ranges, is mounted in sensor head 38. Reflected return energy received by sensor head 38 is transmitted to processing unit 39 by means of a fiber optic cable 40, which is attached to the sensor head, for computer processing to determine and indicate resin-content based on non-absorbed reflected radiation energy.

EXAMPLE I

Resin-Loading of Particles

Example I involves VIS/NIR spectroscopic measurements to determine resin-loading of particles which are to be made into particleboard (PB). Resin-loading for calibration can be varied from 0% to above about 12%; initial moisture content (MC) can be 6%. Spectral data were collected using instrumentation and software as tabulated later herein. The instrument sensor head is connected to a fiber optic bundle. The sensor head is mounted about seven inches above the particle/resin blend. The size illumination and measurement area can be between about a three inch diameter to about a twenty inch diameter on the moving support for the test samples.

Example I was carried out using a rotary table. For calibration, test-samples having known pre-established resin contents were measured. It had been determined that resin-loading is in linear relationship with absorbed radiation of the selected wavelength range(s). The resulting measurements of the pre-determined test samples establish that a linear relationship between absorbed radiation and resin-loaded percentage weights, which is the basis for the linear calibration curve shown later herein.

The turntable simulates a rate of movement on a continuous conveyor system. Although the height of the furnish was not strictly controlled in the lab embodiment, a straight edge can be used to roughly level the surface where the VIS/NIR beam contacts the furnish. The bulk of the measurement was made on 6% initial moisture content (MC) PB furnish.

Figure 4:
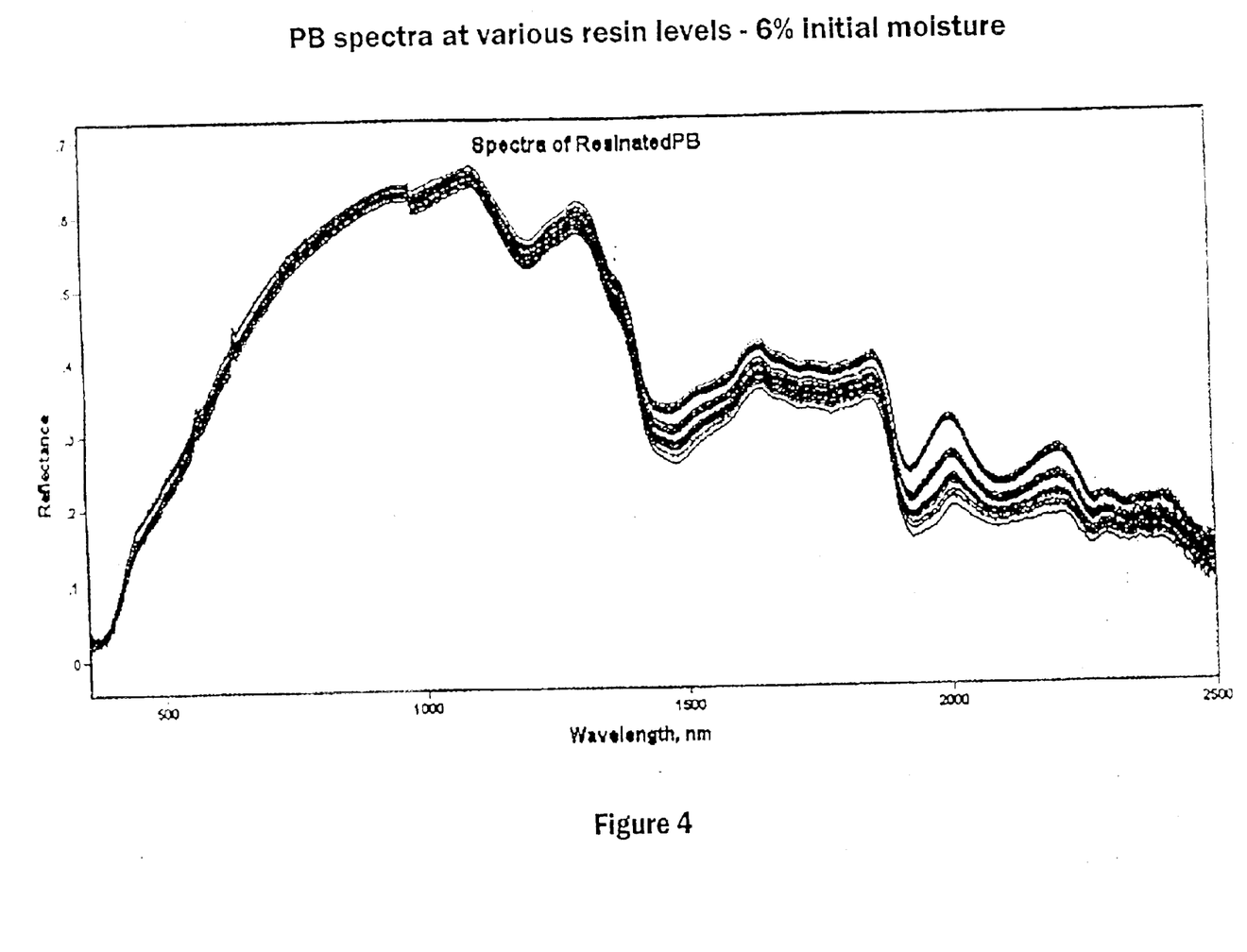
FIGS. 4 and 5 present graphical resin-loading measurement data relating to the particleboard (PB) embodiment of the invention of FIG. 1, and FIGS. 6–8 present graphical resin-loading measurement data relating to the Medium Density Fiberboard (MDF) embodiment of the invention of FIG. 2.

FIG. 4 shows the spectra obtained measuring samples at differing resin loadings for the particulate described above. The data verifies that moisture content (MC) has no significant effect on resin content measurements; measurement can be made with or without removal of the water bands. Based on measurements of actual resin-content values, a coefficient of regression of 0.9974 was obtained.

Figure 5:
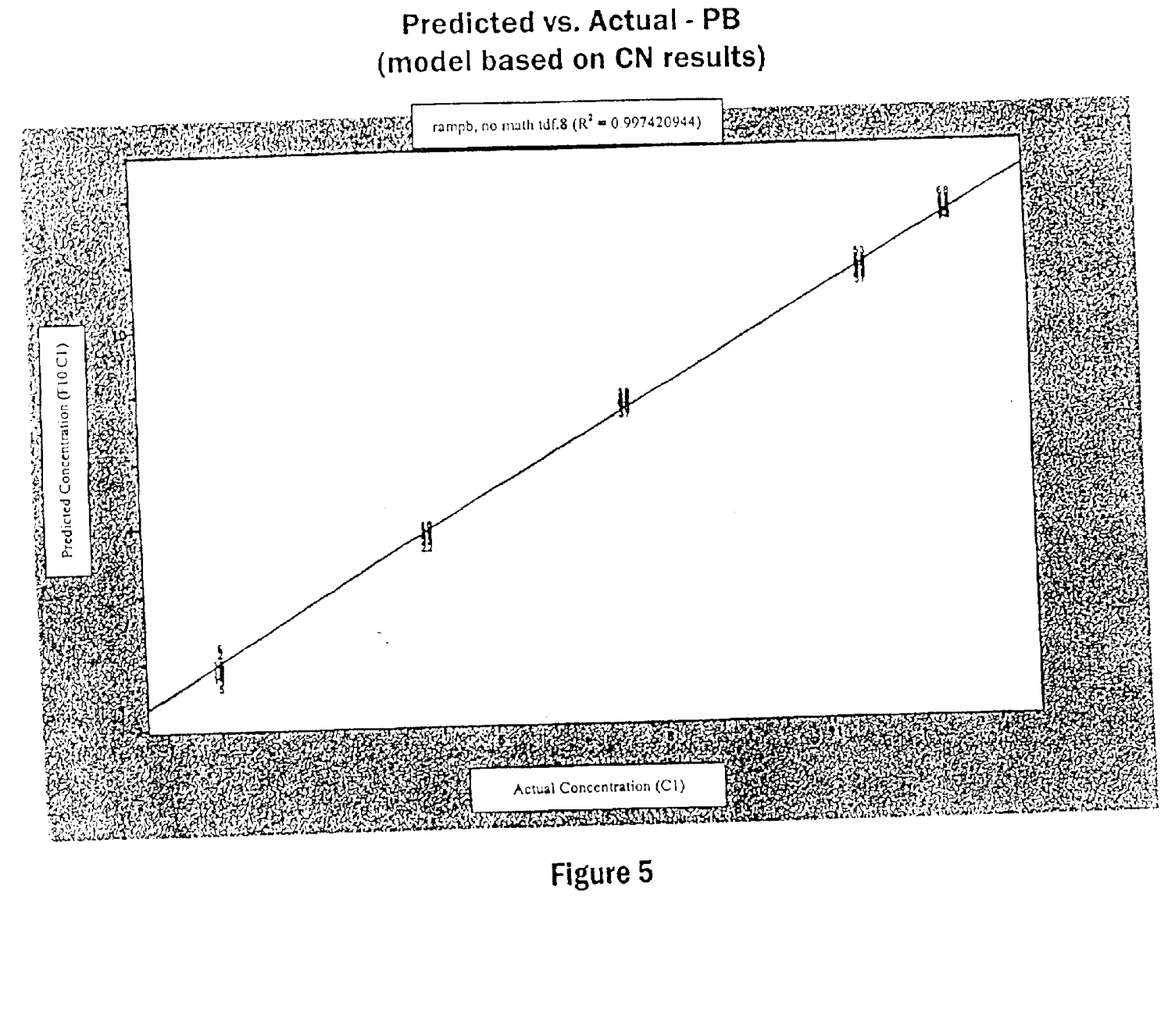

FIG. 5 shows the linear calibration curve resulting from such measurements in which resin-loading percentage weight is linearly related to absorbed radiation energy.

EXAMPLE II

Resin-Loading of Fibers

Example II utilizes VIS/NIR spectroscopic instrumentation for determination of resin-loading of medium density fiberboard (MDF) fibers which are compacted as described earlier. Resin-loading was varied from zero to above about twelve percent; MC was varied from six to ten percent. Spectral data were collected with a sensor head connected to a fiber optic bundle. The sensor head was mounted at a distance of about seven inches above the compacted form. The illumination measurement area covered about a three to about a twenty square inch area. Example II was supported using a rotary turntable. A wavelength range was selected in the 350–2500 nm spectral region. Measurements again verify that moisture content has no significant effect on measurement of resin-loading.

The resin used in Example II was the same UF resin utilized in Example I. Measurements were made on compacted MDF placed on a turntable; rotation at ten rpm was established. As above noted, the turntable was rotated to simulate the travel rate of a continuous conveyor system. The bulk of the measurement was made on six percent MC wood material; but measurements were also carried-out on compacted MDF containing ten percent MC.

Resin levels were pre-established at 0%, 4%, 8% and about 12%. Atomized resin was fed into a blending chamber and applied to the wood fibers from a fluidized resin bed established in the chamber. A Carbon-Nitrogen (CN) static chemical analyzer was used to establish actual resin content of referenced-source test-samples. The sensor head was suspended above the pre-press form at a distance of about seven inches; fiber height of the pre-press forms was not closely monitored, which is similar to production conditions. Non-absorbed reflected VIS/NIR spectral data were obtained and processed by computer to provide resin-content percentage weight.

Figure 6:
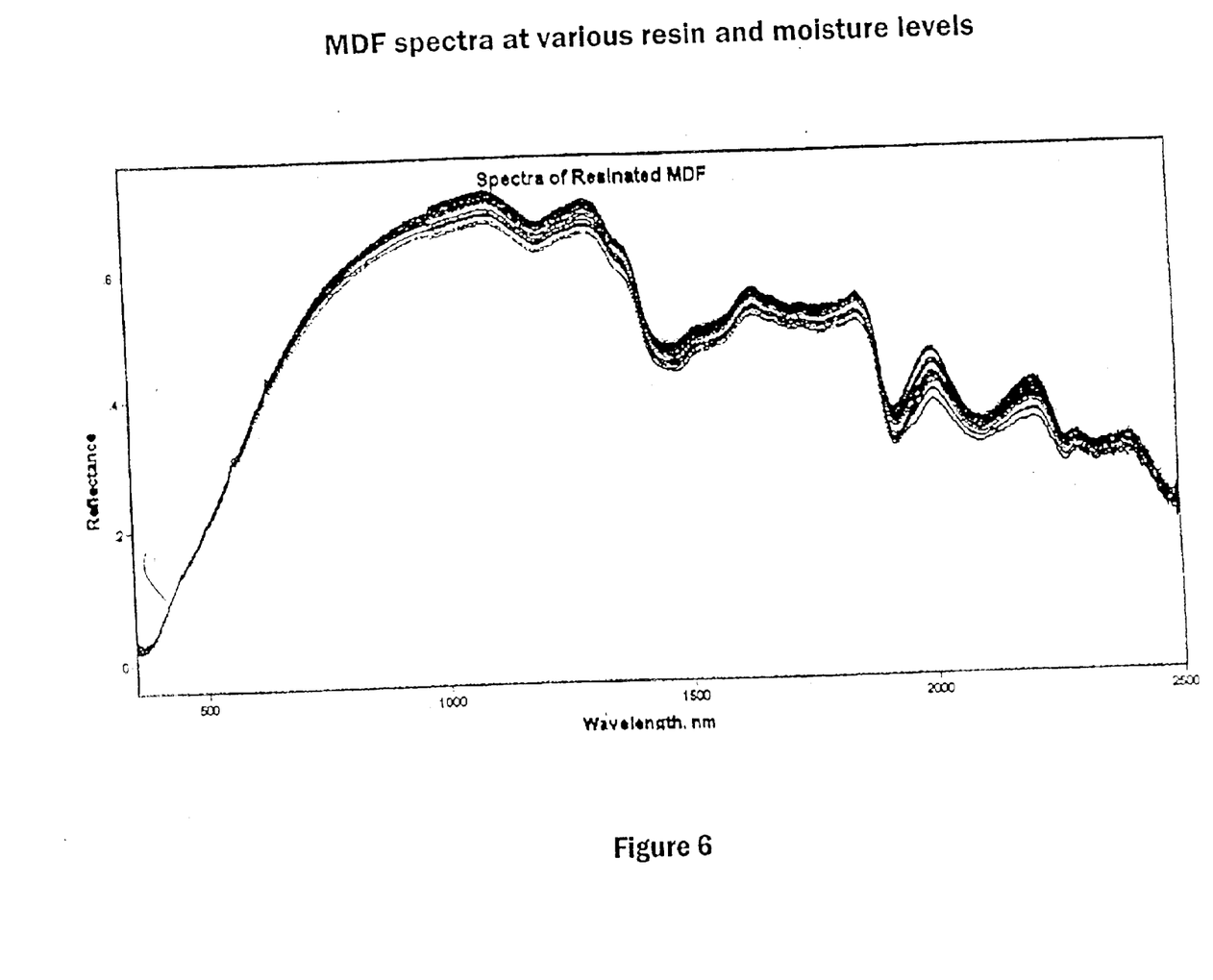

FIG. 6 shows the spectra obtained for different resin-loadings, and at different moisture contents, for resinated MDF fibers. Calibration based on actual pre-established resin-content, and the measured VIS/NIR absorption at selected differing wavelength ranges in the 400–2200 nm region resulted in a linear calibration curve as shown in FIG. 7, which includes water absorption wavelengths.

Figure 7:
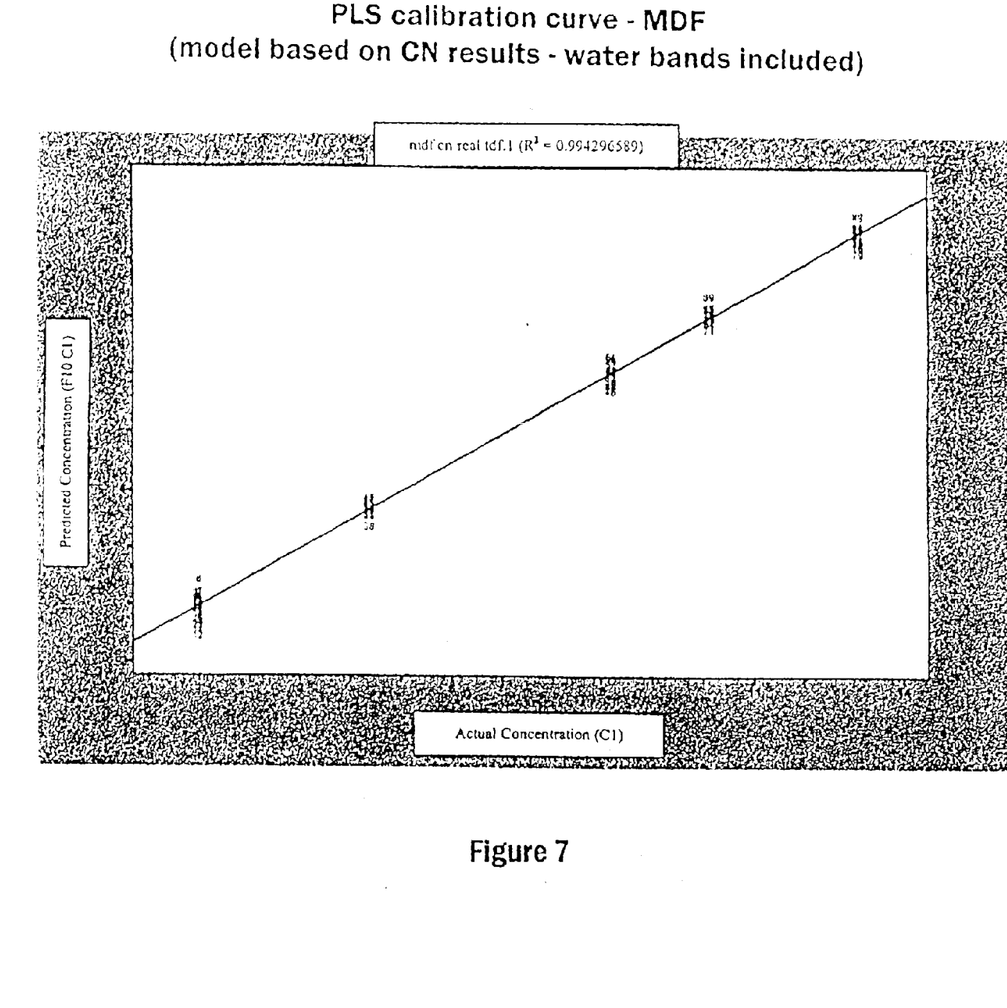
Figure 8:
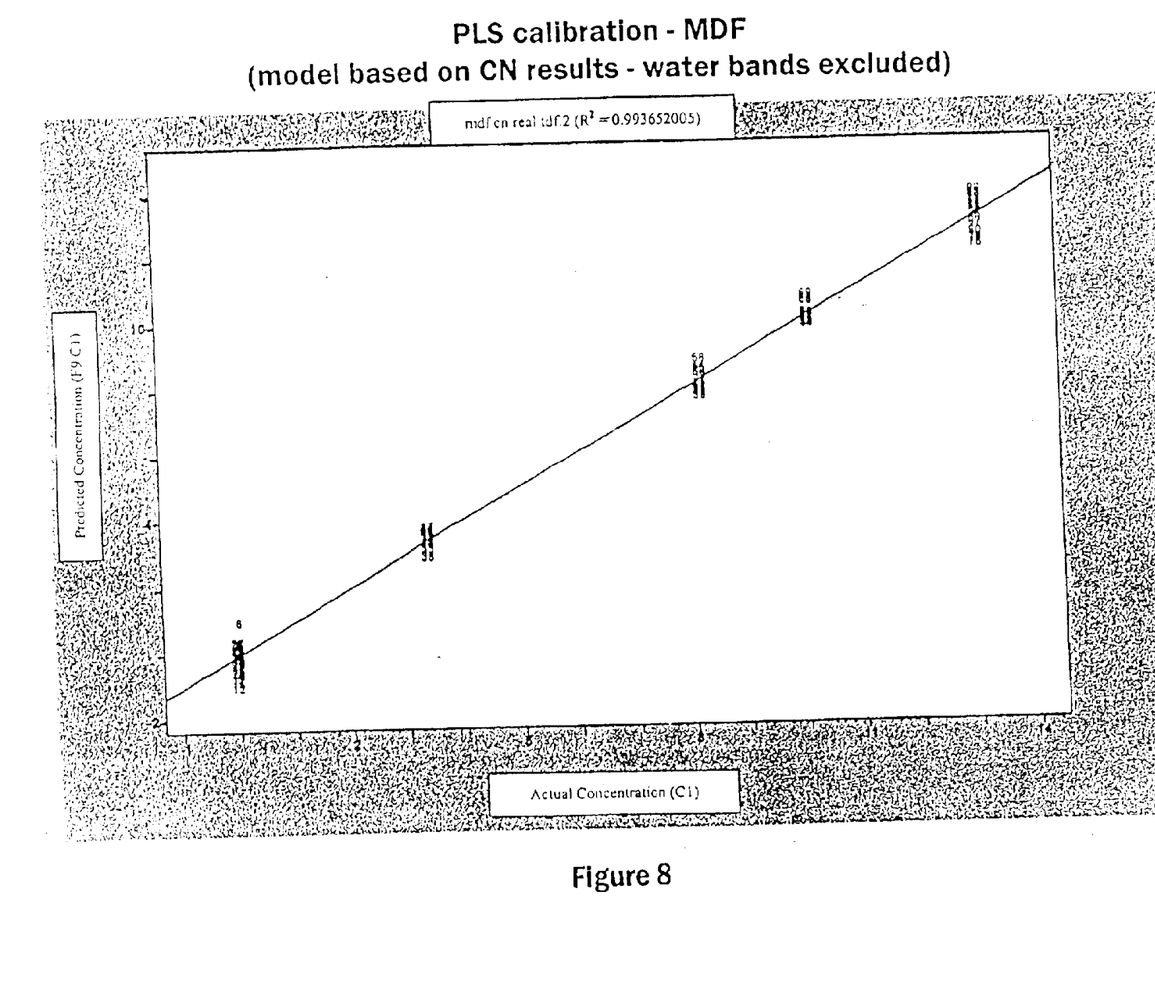

Calibration based on resin absorption, by excluding water absorption wavelength regions of 900–1000 nm, 1400–1450 nm and 1900–1950 nm, is shown in FIG. 8, which is substantially identical to FIG. 7. FIG. 8 shows that moisture content of the wood material, or of the resin, does not have significant effect on resin-loading measurements. Those results eliminate concern with water/moisture content of the substrate, environment, or the like, for effecting monitoring of the resin-content. Also, measurements in accordance with the invention are independent of wood type; the wood is a constant since the changes, if any, being measured are only with respect to the amount of resin.

The resin is selected in a fluid, preferably liquid, state so as to facilitate atomizing for fluidized bed application; some powdered resin can be used provided atomized fluidization is not disturbed. Wax, for water resistance of the composite product, and some other additives, can also be utilized with furnish-type wood materials; provided they can be added without disturbing desired atomizing for the resin-loading fluidized-bed operation of the invention.

Monitoring and measuring processes can also be carried out either including or excluding the wavelength regions measuring moisture content of the resin or wood materials, i.e., 900–1000 nm, 1400–1450 nm and 1900–1950 nm. Accurate results are obtained in absence of measurement of the water wavelength bands.

Spectroscopic Equipment
   Source:
   Analytical Spectral Devices, Inc. (ASD)
   5335 Sterling Drive, Suite A
   Boulder, Colo. 80301
Instrument Name: FIELDSPEC PRO.
Sensors (Arranged in Increasing Order of Price)

| | Wavelength (nm) | Detection Type |
|---|---|---|
| | 350–1050 | Silicon |
| | 1000–1800 | Indium-Gallium-Arsenide; single spectrometer |
| | 1000–2500 | Indium-Gallium-Arsenide; dual spectrometer |
| | 350–2500 | Silicon + Indium-Gallium-Arsenide (photodiode array) |
| Source: | Foss-NIR Systems | |
| | 400–2500 | Lead Sulfide |

Software Processing Equipment
   Source: ASD
   For collecting spectra data

| Name: | LabSpec PRO, version 6.0 |
|---|---|

For measured Data Processing

| Name: | Grams/32 V5 |
|---|---|

Resin

| Type: | Urea Formaldehyde (UF) |
|---|---|
| Name: | CHEMBOND ® 5560 |
| Source: | Dynea, USA |
| | 1600 Valley River Drive |
| | Suite 3900 |
| | Eugene, OR 97401 |

Detailed information on materials, values, apparatus and software have been described for purposes of disclosing the invention. However, the above disclosure can position others to make modifications in those specifics, without departing from the valid scope of protection of the present invention; therefore, the scope of patent protection should be determined from the appended claims, interpreted in the light of the above disclosure.

What we claim as our invention is:

1. Process for utilizing electromagnetic-radiation spectroscopic instrumentation for quantitative measurement of resin-loading of wood-materials during on-line assembly prior to bonding into composite wood-product, comprising
  (A) providing spectroacopic instrumentation including
    (i) a source of electromagnetic irradiation with a wavelength range for penetration of resin-loaded wood material, and
    (ii) sensor means for wavelengths within said wavelength range;
  (B) establishing that a pre-determined linear relationship exists between quantitative resin-loaded percentage weight of said wood materials and absorption of radiation in said wavelength range;
  (C) calibrating said spectroscopic instrumentation for non-invasive quantitative measurement of resin-loading of said wood materials while moving in an assembly line, by
    (i) accurately pre-establishing resin-loading of reference-source test-samples containing wood-materials of a type selected for on-line assembly and which are capable of resin-loaded bonding to produce a composite wood-product,
    (ii) supporting said pre-established resin-loaded test-samples on a conveyance surface capable of establishing a controlled rate of relative movement of said supported test-samples in relation to said instrumentation source and sensor means for measuring resin-loading by measuring non-absorbed radiation reflected by said wood-materials test-samples;
    (iii) establishing said controlled rate of relative movement for said test-samples simulating a selected on-line controlled-rate of movement for said type of resin-loaded wood-materials being directed on-line for assembly, while
    (iv) irradiating said pre-established resin-content test-samples with radiation of said selected range of wavelengths, during said relative movement at said selected controlled rate,
    (v) measuring non-absorbed radiation, reflected by said test-samples with said spectroscopic instrumentation, for calibration purposes, by
    (vi) graphically plotting
      (a) measured resin-loading of said test-samples, by processing non-absorbed energy within said selected range of wavelengths as reflected by said exposed test-samples, versus
      (b) said pre-established resin-loading of said test-samples, so as to verify that instrumentation as calibrated provides a linear relationship between percentage-weight loading of resin and absorbed radiation, for utilization of said instrumentation on-line;
  (D) establishing resin-content of said test-samples so as to present incrementally-progressive resin-loading of wood-materials for respective test-samples, with said resin-loading being selected from the group, consisting of
    (i) percentage weight of resin to weight of wood-material furnish, and
    (ii) extending incrementally in a range of zero percent to above about twelve percent (12%);

(E) establishing relative movement between said test-samples and said irradiation source and sensor means instrumentation by selecting a rotatable conveyance surface capable of being driven at a controlled rotational rate, so as to
  (i) simulate a selected in-line movement rate for resin-loading of said type wood-materials for in-line assembly, so as to enable
  (ii) measuring, at that rate, reflected non-absorbed radiation energy from wood materials of said progressively resin-loaded test-samples;
(F) selecting a wavelength range from the group consisting of
  (i) 350–1050 nm,
  (ii) 1000–1800 nm,
  (iii) 1000–2500 nm, and
  (iv) 400–2500 nm,
wherein said spectroscopic instrumentation includes a full visible-light spectrum lamp for illuminating said test-samples, from which the red portion of said visible light is absorbed by resin-content of said wood-materials.

2. The process of claim 1, including
selecting a wavelength range of about 400 nm to about 2250 nm, and
removing moisture-content absorptive effect from said non-absorbed reflected energy, by removing measurements at wavelengths of
  900 nm to 1000 nm,
  1450 nm to 1500 nm, and
  1900 nm to 2000 nm.

3. Process for utilizing electromagnetic-radiation spectroscopic instrumentation for quantitative measurement of resin-loading of wood-materials during on-line assembly prior to bonding into composite wood-product, comprising
(A) providing spectroscopic instrumentation including
  (i) a source of electromagnetic irradiation with a wavelength range for penetration of resin-loaded wood material, and
  (ii) sensor means for wavelengths within said wavelength range;
(B) establishing that a pre-determined linear relationship exists between quantitative resin-loaded percentage weight of said wood materials and absorption of radiation in said wavelength range;
(C) calibrating said spectroscopic instrumentation for non-invasive quantitative measurement of resin-loading of said wood materials while moving in an assembly line, by
  (i) accurately pre-establishing resin-loading of reference-source test-samples containing wood-materials of a type selected for on-line assembly and which are capable of resin-loaded bonding to produce a composite wood-product,
  (ii) supporting said pre-established resin-loaded test-samples on a conveyance surface capable of establishing a controlled rate of relative movement of said supported test-samples in relation to said instrumentation source and sensor means for measuring resin-loading, by measuring non-absorbed radiation reflected by said wood-material test-samples;
  (iii) establishing said controlled rats of relative movement for said test-samples simulating a selected on-line controlled-rate of movement for said type of resin-loaded wood-materials being directed on-line for assembly, while
  (iv) irradiating said pre-established resin-content test-samples with radiation of said selected range of wavelengths, during said relative movement at said selected controlled rate,
  (v) measuring non-absorbed radiation, reflected by said test-samples with said spectroscopic instrumentation, for calibration purposes, by
  (vi) graphically plotting
    (a) measured resin-loading of said test-samples, by processing non-absorbed energy within said selected range of wavelengths as reflected by said exposed test-samples, versus
    (b) said pre-established resin-loading of said test-samples, so as to verify that instrumentation as calibrated provides a linear relationship between percentage-weight loading of resin and absorbed radiation, for utilization of said instrumentation on-line;
(D) establishing resin-content of said test-samples so as to present incrementally-progressive resin-loading of wood-materials for respective test-samples, with said resin-loading being selected from the group, consisting of
  (i) percentage weight of resin to weight of wood-material furnish, and
  (ii) extending incrementally in a range of zero percent to above about twelve percent (12%);
(E) establishing relative movement between said test-samples and said irradiation source and sensor means instrumentation by selecting a rotatable conveyance surface capable of being driven at a controlled rotational rate, so as to
  (i) simulate a selected in-line movement rate for resin-loading of said type wood-materials for in-line assembly, so as to enable
  (ii) measuring, at that rate, reflected non-absorbed radiation energy from wood materials of said progressively resin-loaded test-samples;
(F) selecting a wavelength range from the group consisting of-
  (i) 350–1050 nm,
  (ii) 1000–1800 nm,
  (iii) 1000–2500 nm, and
  (iv) 400–2500 nm;
wherein said wood materials are furnish-type wood-materials, and said process further includes
  (1) selecting wood materials from the group consisting of
    (a) wood particulate for particleboard (PB), and
    (b) wood fiber for medium density fiberboard (MDF), for
  (2) verifying calibration of said instrumentation for on-line Assembly of said selected wood-material,
  (3) providing for on-line location of spectroscopic measuring instrumentation for,
non-invasive measuring of resin-loading of selected wood material, moving in an assembly line, for subsequent bonding-treatment production of composite wood product, in which
said instrumentation has been calibrated in accordance with the process of claim 1 respectively,
    (a) for particleboard (PB), or
    (b) for medium density fiberboard (MDF),
  (4) controlling resin-loading, of said selected wood-material on-line, by selecting from the group consisting of
    (a) quantitatively-controlled metering of resin introduced for atomized fluidized-bed contact with said selected wood-material moving through said fluidized-bed,
(b) controlling rate of movement of said wood-materials in said fluidized-bed, and
(c) combinations of (a) and (b).

4. The process of claim 3, further including
establishing a rate of movement for resin-loaded wood-materials onto a conveyor surface which is moving at a rate correlated with said rate of movement utilized during said calibration of said spectroscopic instrumentation for measurement of resin-loading.

5. The process of claim 4, including
quantitatively-monitoring resin-loading of said selected wood-material, by measuring resin-loading of said resin-loaded wood-materials, subsequent to delivery from said resin-loading fluidized-bed, while supporting for irradiation with respect to said instrumentation.

6. The process of claim 5, in which
wood particulate is selected for assembly, and
said resin-loaded particulate is measured for resin-loading percentage weight as delivered from said fluidized-bed.

7. The process of claim 5, in which
wood-fibers are selected for assembly; further including
compacting said resin-loaded wood fibers, as delivered from said fluidized-bed, for facilitating measuring resin-loading of said fibers.

8. The process of claim 6 or 7, further including
providing for quantitatively-controlling resin-loading during continuing on-line assembly, by
(i) indicating resin-loading value as measured by said calibrated instrumentation, for
(ii) feedback control of resin-loading, by
(iii) selecting from the group consisting of
(a) quantitatively controlling resin as introduced for contact with said wood-materials,
(b) controlling rate of movement of said wood-materials through said fluidized-bed for delivery on said assembly line, and
(c) combinations of (a) and (b), for
(iv) maintaining a desired uniform resin-loading weight in relation to weight of said wood-material; during on-line assembly.

9. The process of claim 6 or 7, further including
(i) bonding said wood-materials and resin-loading by timed exposure to heat and pressure, so as to
(ii) polymerize said controlled resin-content, producing said composite wood product.

10. Product-by-process composite-wood-product, produced by
treating under heat and pressure said resin-loaded particulate, in which control of resin-loading is carried out in accordance with the process of claim 6, so as to
polymerize said resin production composite-wood particleboard (PB).

11. Product-by-process composite-wood-product produced by
treating under heat and pressure said resin-loaded fibers, with controlled resin-loading of said fibers being carried out in accordance with the process of claim 7, so as to
polymerize said resin producing composite medium density fiberboard (MDF).

* * * * *